(12) United States Patent
West (10) Patent No.: US 8,545,415 B2
(45) Date of Patent: Oct. 1, 2013

(54) PORTABLE ALVEOLAR GAS METER

(75) Inventor: John B. West, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 1987 days.

(21) Appl. No.: 11/569,533

(22) PCT Filed: May 25, 2005

(86) PCT No.: PCT/US2005/018606
§ 371 (c)(1),
(2), (4) Date: Nov. 22, 2006

(87) PCT Pub. No.: WO2005/117700
PCT Pub. Date: Dec. 15, 2005

(65) Prior Publication Data
US 2007/0232950 A1    Oct. 4, 2007

Related U.S. Application Data (60) Provisional application No. 60/574,400, filed on May 26, 2004.

(51) Int. Cl.
*A61B 5/08*    (2006.01)

(52) U.S. Cl.
USPC ............................ 600/532; 600/543; 73/23.3

(58) Field of Classification Search
USPC ................. 600/532, 529, 531, 533, 538, 543; 73/23.3
See application file for complete search history.

(56) References Cited

U.S. PATENT DOCUMENTS

| | | | | |
|---|---|---|---|---|
| 4,034,743 A * | 7/1977 | Greenwood et al. | .......... | 600/538 |
| 4,090,078 A * | 5/1978 | Heim | ............................ | 250/343 |
| 4,368,740 A * | 1/1983 | Binder | ......................... | 600/531 |
| 4,440,177 A * | 4/1984 | Anderson et al. | ............. | 600/532 |
| 5,465,728 A * | 11/1995 | Phillips | ........................ | 600/543 |
| 5,971,934 A * | 10/1999 | Scherer et al. | ................ | 600/526 |
| 6,142,950 A * | 11/2000 | Allen et al. | .................... | 600/529 |
| 6,402,697 B1 * | 6/2002 | Calkins et al. | ................ | 600/532 |
| 6,575,918 B2 * | 6/2003 | Kline | ............................ | 600/532 |
| 6,582,376 B2 * | 6/2003 | Baghdassarian | .............. | 600/543 |
| 6,599,253 B1 | 7/2003 | Baum et al. | | |

(Continued)

OTHER PUBLICATIONS

Maret, K.H., "Automatic mechanical alveolar gas sampler for multiple-sample collection in field," Journal of Applied Physiology: Respiratory, Environmental and Exercise Physiology, 56(5):1436-1438, May 1984.

*Primary Examiner* — Navin Natnithithadha
(74) *Attorney, Agent, or Firm* — Perkins Coie LLP (57) ABSTRACT

A portable alveolar gas measurement device and method of determining at least one alveolar gas level are disclosed. The device includes a structure that receives a sample portion of breath, and a gas sensor in communication with the structure that detects a gas level of a gas within the sample portion and provides a first signal indicative of the level. The device further includes circuitry coupled at least indirectly to the gas sensor, where the circuitry receives at least one of the first signal and a second signal related to the first signal, and where the circuitry provides at least some assistance in determining whether a portion of information provided by the at least one signal is used as an indication of an alveolar gas level. Additionally, the device includes an output device coupled to the circuitry that provides an output indicative of the first alveolar gas level.

38 Claims, 8 Drawing Sheets

(56) References Cited

U.S. PATENT DOCUMENTS

| | | |
|---|---|---|
| 6,612,306 B1 | 9/2003 | Mault |
| 6,955,652 B1 * | 10/2005 | Baum et al. .................. 600/532 |
| 7,282,032 B2 * | 10/2007 | Miller ........................... 600/538 |
| 7,473,229 B2 * | 1/2009 | Webber ......................... 600/532 |
| 7,699,788 B2 * | 4/2010 | Kuck et al. .................... 600/532 |
| 7,914,460 B2 * | 3/2011 | Melker et al. ................. 600/532 |

* cited by examiner

O₂ ANALYZER VS. MGA 1100
5/5/2004

| MGA1100 | O₂ ANALYZER | |
|---|---|---|
| 0.0 | 0.0 | 100% $N_2$ |
| 20.9 | 159.0 | ROOM AIR |
| 7.0 | 56.3 | |
| 8.0 | 64.0 | REGRESSION, RUN 1 |
| 9.3 | 74.2 | (GAS TANK VALUES ONLY): |
| 10.1 | 81.3 | SLOPE     0.124959 |
| 11.0 | 88.4 | INTERCEPT     -0.023 |
| 11.8 | 94.9 | $R^2$     0.999964 |
| 12.9 | 103.1 | |
| 14.1 | 113.2 | |
| 15.1 | 121.4 | |
| 15.9 | 127.5 | |
| 17.2 | 137.5 | |
| 18.1 | 145.2 | |
| 19.2 | 154.0 | |
| 20.0 | 159.8 | |
| 20.7 | 165.8 | |
| 0.0 | 0.1 | 100% $N_2$ |
| 20.9 | 159.7 | ROOM AIR |
| | | |
| 20.8 | 165.7 | |
| 20.0 | 159.3 | REGRESSION, RUN 2 |
| 19.0 | 151.6 | (GAS TANK VALUES ONLY): |
| 18.1 | 144.2 | SLOPE     0.125745 |
| 17.2 | 137.3 | INTERCEPT     -0.038 |
| 15.8 | 125.8 | $R^2$     0.999969 |
| 14.9 | 118.6 | |
| 14.1 | 112.1 | |
| 12.8 | 102.0 | |
| 11.7 | 93.6 | |
| 10.9 | 86.8 | |
| 10.1 | 80.6 | |
| 9.3 | 74.1 | |
| 8.0 | 64.4 | |
| 7.0 | 56.4 | |
| 0.0 | 0.0 | 100% $N_2$ |
| 20.9 | 159.7 | ROOM AIR |

PORTABLE ALVEOLAR GAS METER

CROSS-REFERENCE TO RELATED APPLICATIONS

This application claims the benefit of U.S. provisional patent application No. 60/574,400 entitled "Portable Alveolar Gas Meter" filed on May 26, 2004, which is hereby incorporated by reference herein.

STATEMENT REGARDING FEDERALLY SPONSORED RESEARCH OR DEVELOPMENT

FIELD OF THE INVENTION

The present invention relates to medical test equipment and other testing devices used to perform tests on human beings and, more particularly, to devices used to measure chemical concentrations occurring in the human body.

BACKGROUND OF THE INVENTION

Obtaining measurements of various chemicals in the human body is desirable in a variety of situations. In particular, the measurement of oxygen ($O_2$) in the body can be an important indication of whether the body is properly receiving and processing oxygen, and thus can be indicative of disease or trauma, among other things. Such information can be of use in a variety of environments, including for example in an operating room or in an ambulance, in physical-fitness or exercise environments, as well as in high-altitude environments or underwater environments (e.g., as experienced by mountain climbers, miners, and divers employing scuba gear).

In the hospital setting, various tests exist for measuring a patient's oxygen levels. One conventional test involves measuring the oxygen saturation of hemoglobin in the patient's bloodstream by way of a pulse oxymeter. While conveniently small and portable, this device is limited insofar as the data it provides cannot be used to determine whether a patient is hyperventilating or underventilating. Additionally, this device is not particularly helpful in some situations such as high-altitude situations, because changes in oxygen levels in a person's bloodstream can vary nonlinearly in relation to oxygen levels that are occurring in the person's lungs (due to a nonlinear dissociation curve), such that measurements of the oxygen levels in the person's bloodstream may not provide a clear or accurate indication of the oxygen levels in the person's lungs.

Pulse oxymeter tests are not the only type of test that currently exists that can be employed to determine oxygen levels in a patient. Direct measurements of oxygen gas levels and/or other gas levels deep within a person's lungs (e.g., within the alveoli of the lungs) also can be a useful measure of oxygenation of the lung and thus be useful in assessing one of the links in the chain of oxygen delivery to body tissues. However, although the usefulness of measuring gas levels deep within a person's lungs— or "alveolar gas" levels—has been recognized for decades, conventional techniques for testing such alveolar gas levels are slow in operation and difficult to use.

In particular, conventional devices used to measure alveolar gas levels, such as those employed in some anesthetic machines, are undesirable insofar as those devices typically are large, cumbersome and not portable. Consequently, such devices are not easily employed in environments outside a given hospital operating room or pulmonary function laboratory. Further, although there do exist some conventional devices for measuring gas levels in lungs that are portable, these devices are incapable of distinguishing the alveolar gases existing deep within a patient's lungs from other "mixed gases" that emanate from the bronchial passages of the patient, as well as distinguishing the alveolar gases from the outside atmosphere.

For example, specifically in the context of physical-fitness/exercise, a portable oxygen consumption measuring device has been developed that can be carried on a person's back, namely, the Jaeger Oxycon Mobile by VIASYS Healthcare GmbH of Hoechberg, Germany. This device is not intended to measure alveolar gas but instead is intended to measure the mixed gases emanating from the bronchial passages of the patient, which typically have significantly different levels of oxygen, carbon dioxide, and other gases than exist within the alveoli. Also for example, while breathalyzer devices have been developed for sensing alcohol on the breath of drunk drivers, these devices again are incapable of localizing alveolar gases from the mixed gases of the bronchial passages and, in any event, cannot measure alveolar oxygen and carbon dioxide gas levels.

In view of the value of information regarding alveolar gas levels, and in view of the inadequacies of conventional techniques for determining such gas levels within the human body, it therefore would be advantageous if a new, portable/mobile (possibly hand-held) device for measuring alveolar gas levels such as oxygen and/or carbon dioxide levels (among others) could be developed. In particular, it would be advantageous if such a new, portable device could be utilized by a patient alone or with a technician/physician to quickly measure such alveolar gas levels.

Additionally, it would be advantageous if such a new device could be easily operated such that substantially accurate data concerning the concentration(s) of alveolar gas(es) of interest could be obtained. More particularly, it would be advantageous if the data obtained using the device was substantially accurate notwithstanding the existence of mixed gases within the bronchial passages of a subject's lungs, and notwithstanding differences between the characteristics of the air of the atmosphere relative to the alveolar gases. It further would be advantageous if this new device was robust, self-contained, light in weight, and inexpensive to manufacture.

BRIEF SUMMARY OF THE INVENTION

The present inventor has recognized that a portable alveolar gas level measuring device would be of significant value in a variety of hospital, paramedic, fitness/exercise, high-altitude and other environments. The present inventor further has recognized that, insofar as certain compact, high-sensitivity, accurate, and rapidly operating gas level sensors for gases such as oxygen and carbon dioxide (among others) have recently been developed, it would be possible to create a portable device employing one or more of those sensors allowing for rapid, accurate gas level measurements. Additionally, the present inventor has realized that it would be possible to configure such a portable device so as to obtain accurate alveolar gas level information that was not substantially corrupted by bronchial mixed gases or the gas composition of the outside atmosphere in a number of different ways, depending upon the embodiment.

In certain embodiments, for example, it would be possible to mechanically localize alveolar gas being expired by a patient/subject in relation to other mixed gases expired by the patient and/or the outside air through the use of a special breath receiving structure that isolated a portion of the patient's expired breath that was representative of alveolar gases. In other embodiments, also for example, it would be possible to monitor the gas levels in a patient's breath over a period of time and then determine, based upon analysis of the time-varying data, the characteristics of the alveolar gases in particular. Further, the present inventor has recognized that a variety of implementations are possible for such a portable device, including for example implementations in which data is provided to, processed by, and displayed on a handheld computer.

In particular, in at least some embodiments, the present invention relates to a portable alveolar gas measurement device. The device includes a structure that receives a sample portion of breath, and a first gas sensor in communication with the structure that detects a first gas level of a first gas within the sample portion and provides a first signal indicative of the first gas level. The device further includes circuitry coupled at least indirectly to the first gas sensor, where the circuitry receives at least one of the first signal and a second signal that is related to the first signal, and where the circuitry provides at least some assistance in determining whether a portion of information provided by the at least one signal is used as an indication of a first alveolar gas level. Additionally, the device includes an output device coupled to the circuitry that provides an output indicative of the first alveolar gas level as determined at least in part with the assistance of the circuitry.

Further, the present invention in at least some embodiments relates to a method of determining at least one alveolar gas level of a human subject. The method includes transporting a portable device for determining the at least one alveolar gas level from a first location to a second location proximate the human subject, receiving a breath of the human subject within a receiving structure of the device to obtain a sample portion of the breath, and sensing a first gas level associated with the sample portion. The method also includes providing a signal representative of the sensed first gas level, and providing an output based at least indirectly upon the signal, wherein at least a part of the output is indicative of a first alveolar gas level of the human subject.

Additionally, the present invention in at least some embodiments relates to an apparatus for determining at least one alveolar gas level. The apparatus includes a housing, a gas sensing device supported within the housing, and a receiving structure capable of receiving breath and coupled to the gas sensing device by a sampling passage. The apparatus further includes means for processing and outputting information based upon at least one signal provided by the gas sensing device as a result of exposure of the gas sensing device to at least a portion of the breath. The means for processing and outputting at least one of identifies and assists in the identification of alveolar gas level information included within at least one of the signal and the output information, and the apparatus is configured to be portably moved among a plurality of locations.

DETAILED DESCRIPTION OF THE PREFERRED EMBODIMENT

Figure 1:
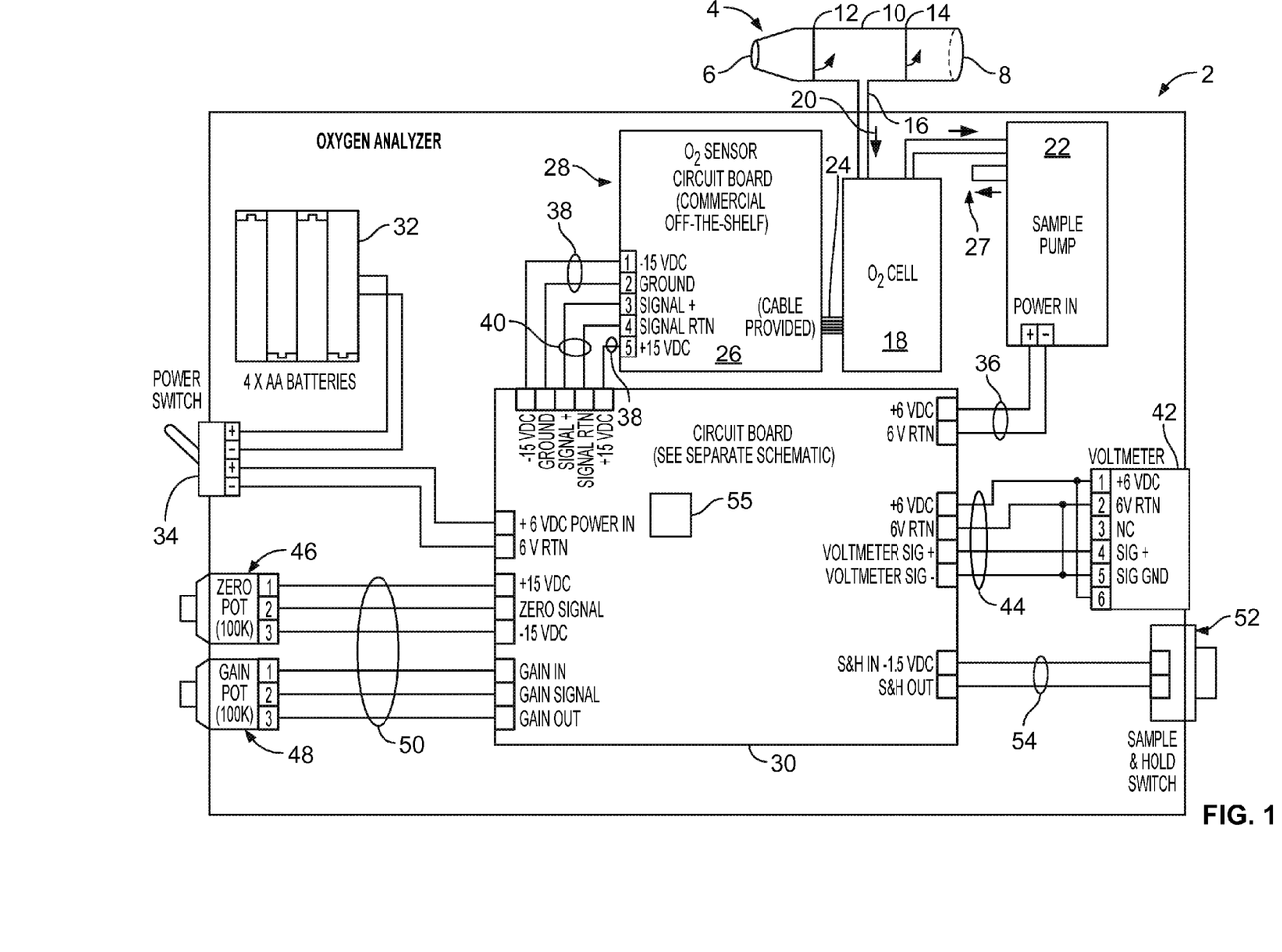
FIG. 1 is a schematic diagram showing components of an exemplary portable alveolar gas meter in accordance with one embodiment of the present invention.

Referring to FIG. 1, a schematic is provided showing components of one exemplary embodiment of a portable device 2 that is capable of being used to measure gas levels existing deep within a human patient's/subject's lungs, for example, "alveolar gas" levels. In the present embodiment, the portable device 2 is shown to be capable of only determining oxygen ($O_2$) gas levels, but in alternate embodiments the portable device is capable of sensing other alveolar gas levels such as carbon dioxide ($CO_2$) levels instead of, or in addition to, oxygen gas levels. In particular, as discussed below with reference to FIG. 5-6, a second exemplary embodiment of a portable device is capable of determining both oxygen and carbon dioxide levels.

As shown in FIG. 1, the portable device 2 includes a receiving structure 4 into which a patient/subject blows in order to allow the portable device to detect alveolar gas levels. In the embodiment shown, the receiving structure 4 is a tubular structure having an inlet 6, an outlet 8, and a sampling space 10 inside the receiving structure between the inlet and outlet. Additionally, the receiving structure 4 has first and second valves 12 and 14, respectively, which are positioned between the inlet 6 and the sampling space 10 and between the sampling space and the outlet 8, respectively. The first and second valves 12, 14 each are designed to open in only one direction allowing flow in only one direction, namely, from the inlet 6 toward the outlet 8, and preventing flow in the opposite direction from the outlet to the inlet. The valves 12, 14 can be any of a variety of types of valves that would allow flow in one direction from the inlet 6 toward the outlet 8 but not in the opposite direction, for example, check valves.

Further as shown, the sampling space 10 is coupled by way of a channel 16 to an oxygen sensor cell (or simply oxygen cell) 18. Gases within the sampling space 10 are pulled into the oxygen cell 18 as indicated by an arrow 20 due to pressure applied by (or a vacuum created by) a pump 22 coupled to the oxygen cell 18. Gases passing through the oxygen cell 18 and then the pump 22 then exit the pump at an outlet 27. The oxygen cell 18 further is electrically coupled, e.g., by way of a cable 24, to an oxygen sensor circuit 26. The oxygen sensor circuit 26 converts signals from the oxygen cell 18 into voltage levels indicative of the oxygen gas levels detected by the oxygen cell. The oxygen cell 18 and oxygen sensor circuit 26 in combination with one another form an overall oxygen sensing device 28.

Although not required, in certain embodiments the channel 16 can include or be formed by a drying tube commercially available from Perma Pure LLC of Toms River, N.J. Use of such a drying tube, which would remove some or all water vapor from the gases communicated through the channel 16, could enhance the capability of the oxygen cell 18 to detect oxygen gas levels (or, in alternate embodiments, enhance the sensing of other gases by other sensing devices as well).

Although a variety of different oxygen sensing devices could be employed in the present embodiment or other embodiments, in one embodiment the oxygen sensing device 28 can be a 2-Year Ultra Fast Oxygen (UFO-130-2) sensor manufactured by Teledyne Analytical Instruments of the City of Industry, Calif. Also, in the present embodiment, the sensed oxygen gas level is in particular indicative of a partial pressure of oxygen gas ($PO_2$). In other embodiments of the portable device in which carbon dioxide is sensed instead of oxygen, a corresponding small $CO_2$ sensor could be employed in place of the oxygen sensing device 28, for example, the Jaeger HCS $CO_2$ sensor manufactured by VIA-SYS Healthcare GmbH of Hoechberg, Germany or the Microstream® $CO_2$ sensor manufactured by Oridion Medical Inc. of Needham, Mass. (or comparable sensor).

Figure 5:
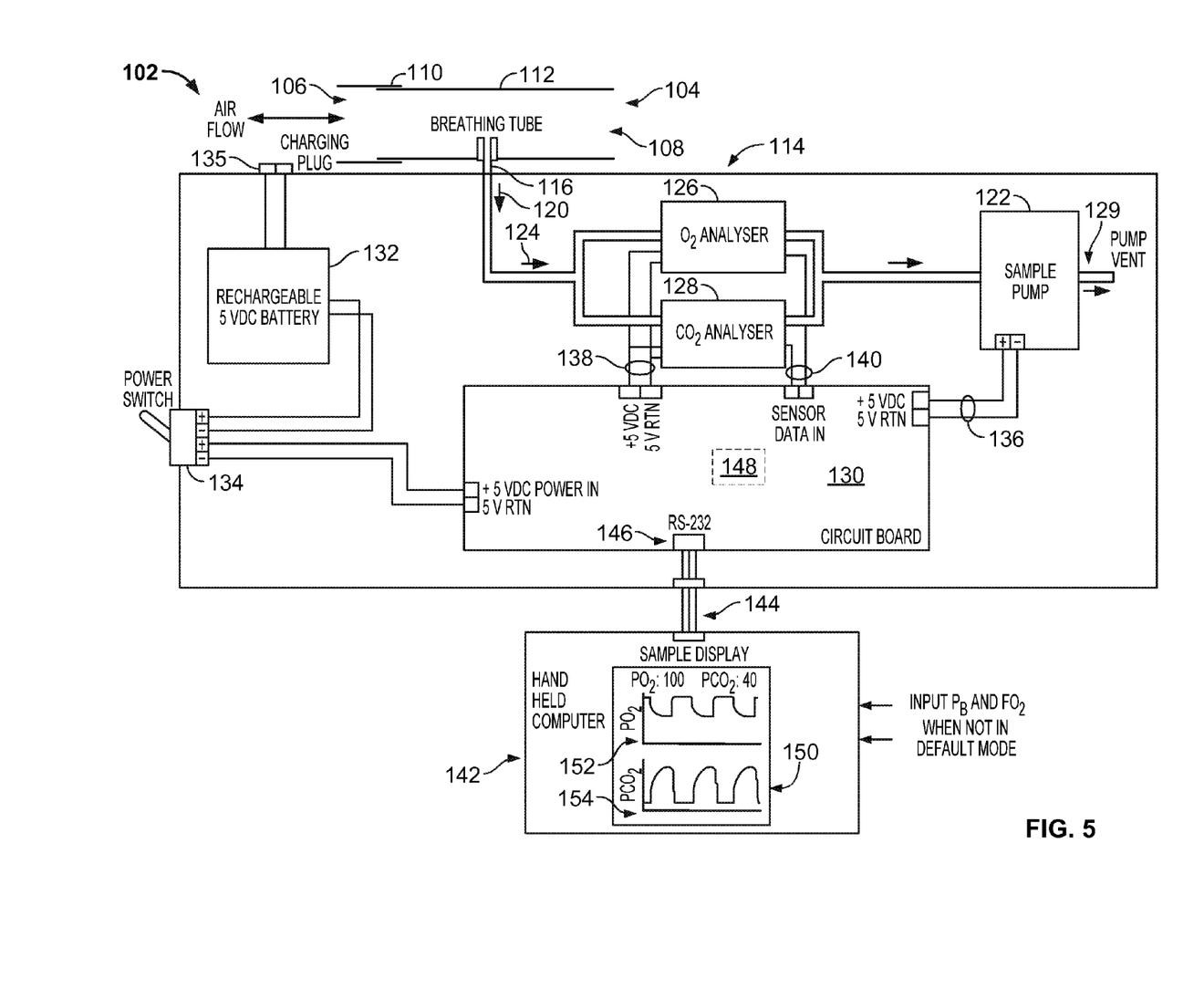
FIG. 5 is a schematic diagram showing components of an additional exemplary portable alveolar gas meter in accordance with another embodiment of the present invention, which is different from that of FIGS. 1-3.
Figure 6:
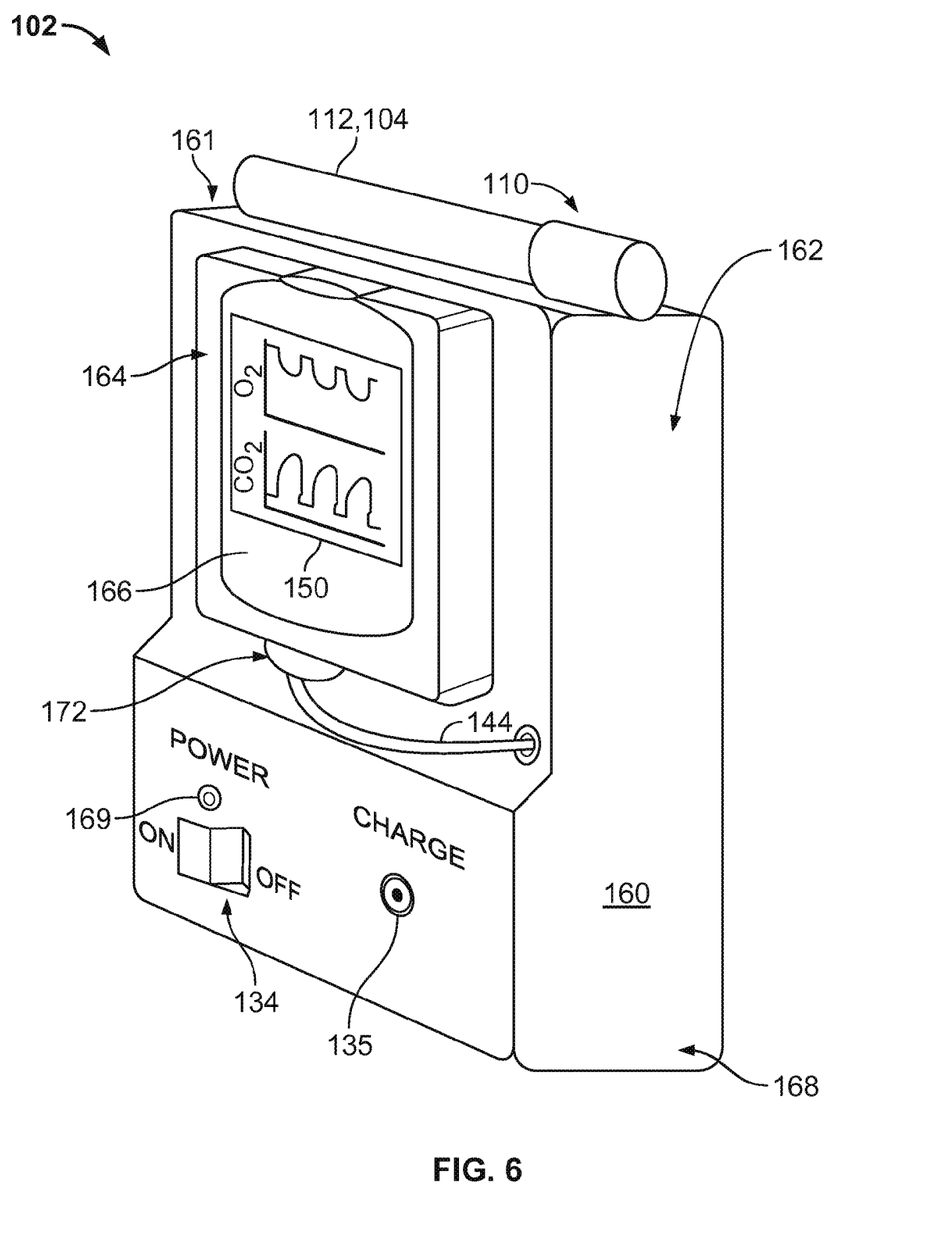
FIG. 6 is a front, perspective view of an exemplary exterior structure of the additional exemplary portable alveolar gas meter of FIG. 5.

Because the amount of carbon dioxide within a person's lungs is relatively inversely proportional to the amount of oxygen in the person's lungs, certain embodiments of the present invention can also utilize carbon dioxide information to calculate oxygen gas levels within the lungs, and vice-versa. Similarly, certain embodiments of the present invention can include multiple sensing devices for sensing multiple different gases including both oxygen or carbon dioxide and/or gases other than oxygen or carbon dioxide. FIG. 5-6 as discussed in further detail below concern another exemplary embodiment of the invention in which oxygen and carbon dioxide are both sensed.

The oxygen sensing device 28 is coupled to a circuit board 30 of the portable device 2. As shown, the portable device 2 can employ one or more batteries 32 such as four AA sized batteries to power the circuit board 30, which in turn provides power to each of the sample pump 22 and the oxygen sensing device 28. Power to these devices from the batteries 32 can be switched on and off by a user by way of a power switch 34 coupled between the batteries 32 and the circuit board 30. As shown, the circuit board 30 relays power to the sample pump 22 by way of power lines 36 and to the oxygen sensing device 28 by way of power lines 38.

The circuit board 30 also is capable of receiving first (voltage) signals by way of communication links 40 from the oxygen sensing device 28 that are indicative of the oxygen levels sensed by the oxygen cell 18 as processed by the oxygen sensor circuit 26. Upon receiving this information in the form of the first signals, the circuit board 30 can further process that information, before resulting output information is communicated to an output device such as a voltmeter 42 by way of additional communication links 44. The voltmeter 42, which in the present embodiment is a digital voltmeter (albeit an analog voltmeter can also be used), is calibrated to specify the sensed oxygen gas level (e.g., the partial pressure of oxygen gas that is measured, $PO_2$) directly in millimeters of mercury.

In alternate embodiments, the output signal(s) provided from the circuit board 30 could be provided to other output devices. For example, instead of or in addition to being coupled to the voltmeter 42, the communication links 44 (or additional communication links) could be coupled to an output port of the portable device 2, which in turn could be coupled to a cable leading to a computer or other device at which the output signal information could be stored, processed or otherwise utilized. As discussed below with reference to FIGS. 5-6, such other device could be, for example, a handheld computer. Also, the portable device 2 could include a wireless transmitter that received the output signal(s) from the circuit board 30 and in turn transmitted those signals to one or more other devices such as a cellular telephone or a remote device (e.g., a remote database).

Depending upon the embodiment, other devices for displaying or otherwise outputting gas level information can also be used in place of or in addition to the voltmeter 42. For example, if the detected oxygen levels are above or below a certain threshold, a warning light or noise could be displayed or sounded. Also for example, and as discussed in more detail below with reference to FIG. 5-6, in some embodiments the data can be output in a graphical manner.

The processing performed by the circuit board 30 can vary depending upon the embodiment. In the present embodiment, the circuit board 30 is configured to be variable in its operation based upon user settings or commands. In particular, the processing performed by the circuit board 30 varies depending upon a user's settings of first and second potentiometers 46 and 48, respectively, which are coupled to the circuit board 30 by way of links 50. Depending upon the settings of the potentiometers 46,48, a user can modify a zero setting or gain factor utilized by the circuit board 30 in its processing. Also in the present embodiment, the output signal(s) output by the circuit board 30 to the voltmeter 42 are representative of the measured oxygen gas levels at specific times when a sample and hold switch 52 is pressed. Pressing of the switch 52 causes sample and hold signals to be communicated from the switch to the circuit board by way of links 54 and in turn causes information based upon the values of the first signals provided on the communication links 40 at these times to be stored in a memory device 55.

Figure 2:
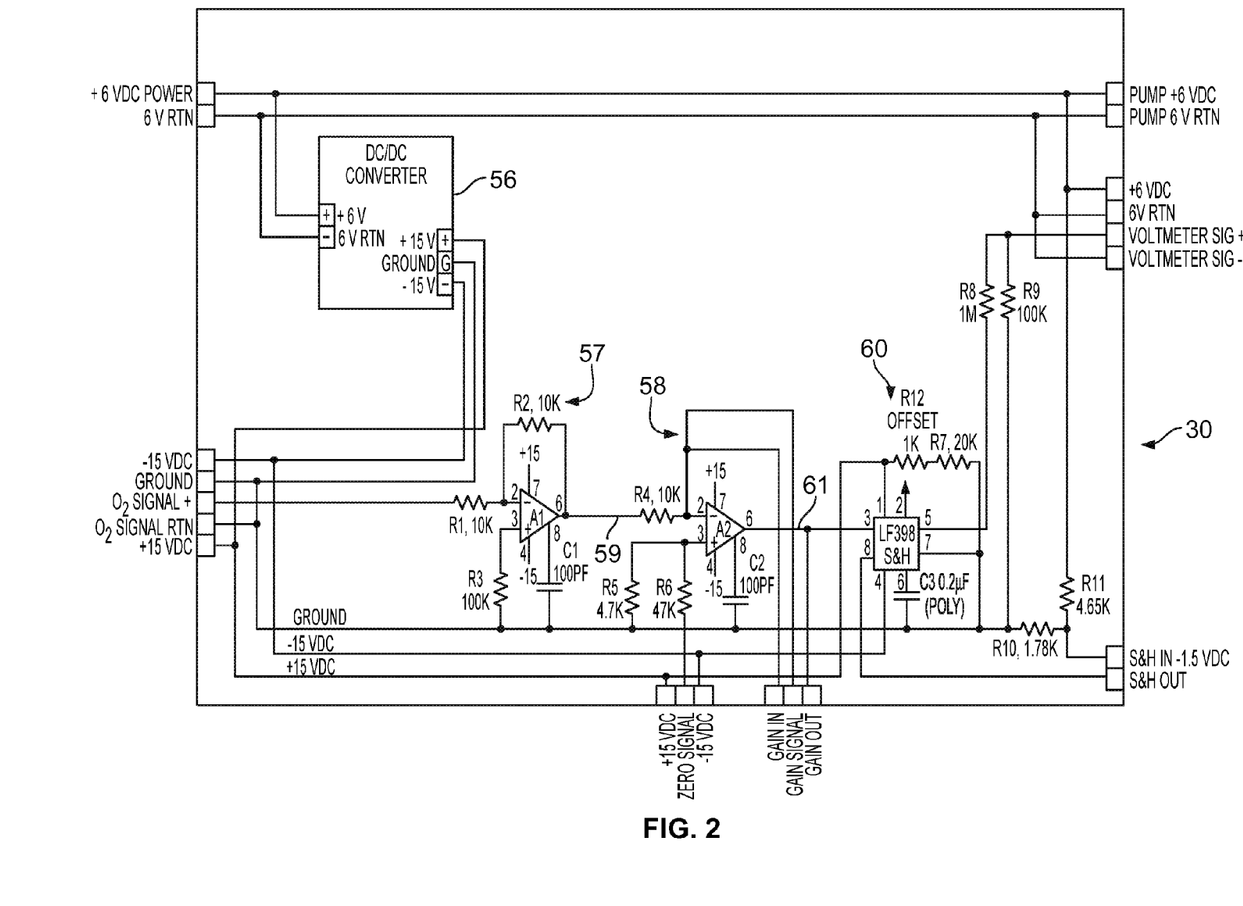
FIG. 2 is a schematic diagram showing exemplary components of a circuit board of the meter of FIG. 1.
Figure 3A:
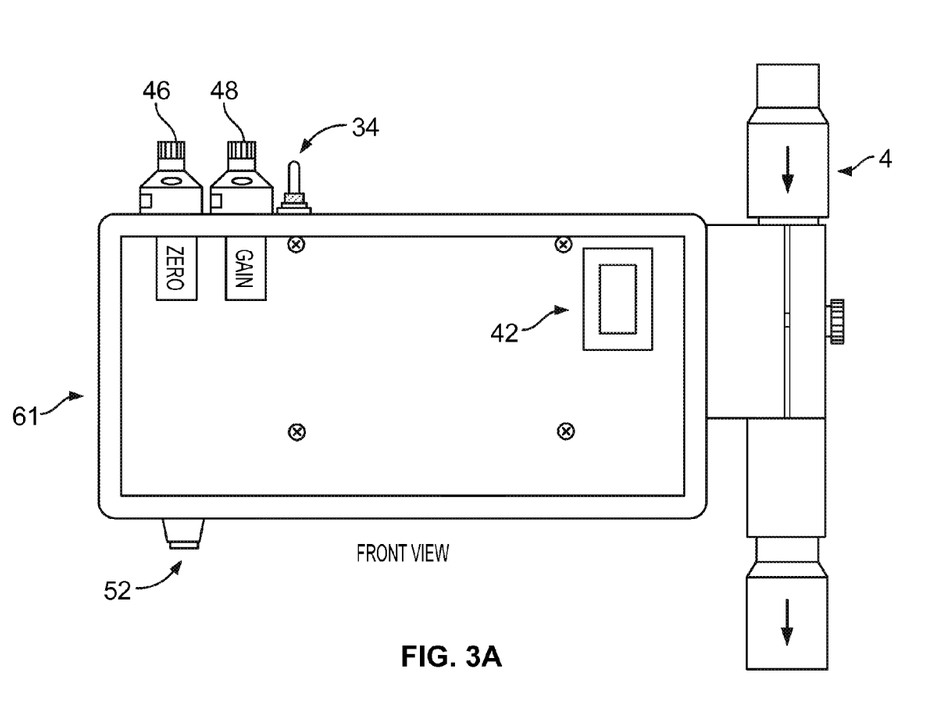
FIGS. 3A, 3B, 3C, 3D and 3E respectively provide front elevation, left side elevation, right side elevation, bottom plan and top plan views of the exemplary meter of FIGS. 1 and 2.
Figure 3B:
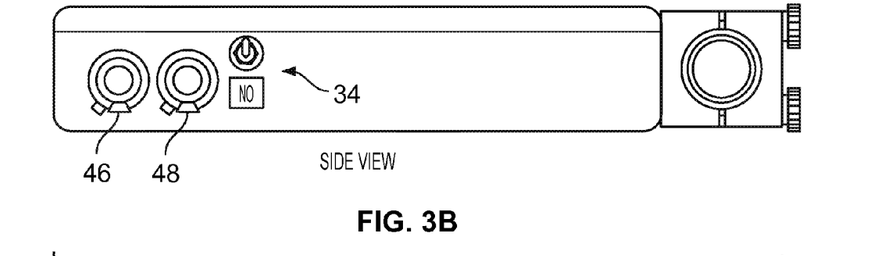
Figure 3C:
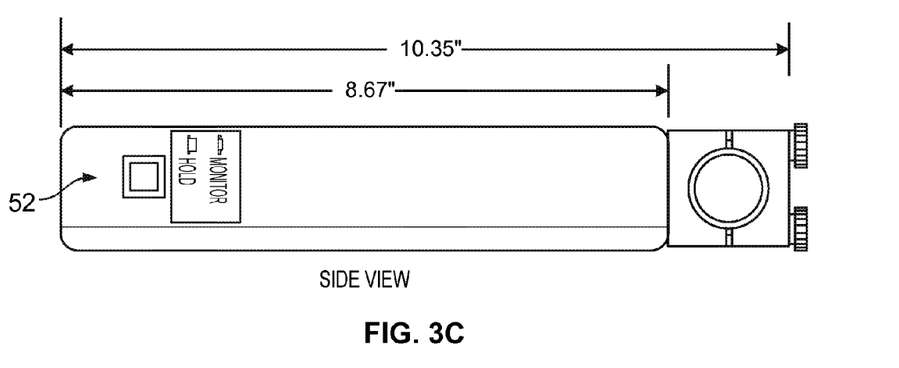
Figure 3D:
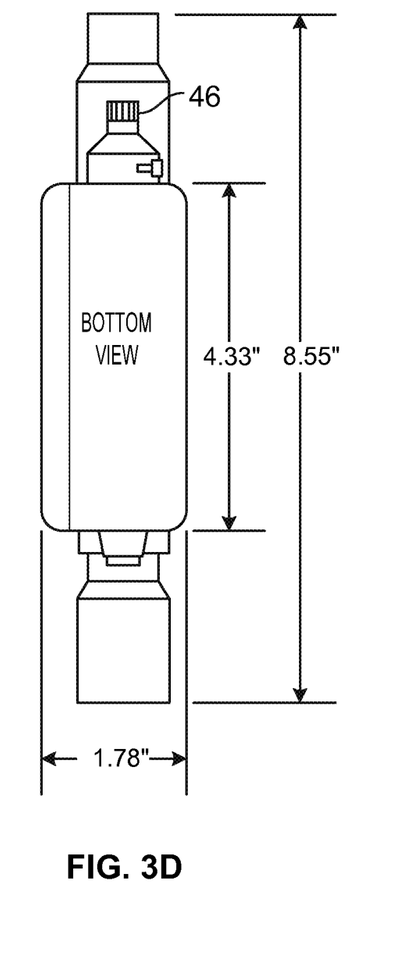
Figure 3E:
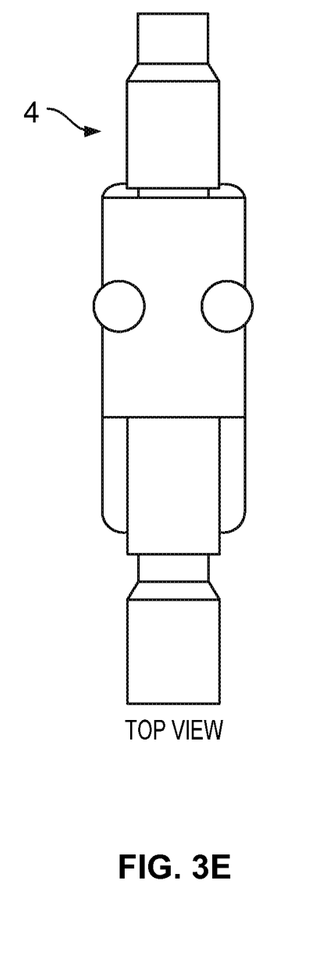

A variety of circuit components can be used within the circuit board 30 depending upon the embodiment. Referring additionally to FIG. 2, in the present embodiment the circuit board 30 includes a DC/DC converter 56 that converts the 6 Volt power from the batteries 32 into 15 Volt power for provision to other components within the circuit board as well as to the oxygen sensing device 28 and to the potentiometers 46,48. The 6 Volt power from the batteries 32 is also provided, without further conversion, from the batteries 32 to the pump 22 and to the voltmeter 42 by way of the circuit board 30.

Additionally, the circuit board 30 includes two (or, in other embodiments, possibly one or more than two) operational amplifier circuits 57 and 58. The operational amplifier circuits 57,58, which are series-connected, receive the first signals via the communication links 40 from the oxygen sensing device 28 and serve to process the signals from the oxygen sensing device in various manners. In the embodiment shown, the operational amplifier circuit 57 acts as a buffer that receives the first signals and in turn outputs second signals by way of a connection 59 to the other operational amplifier circuit 58. As shown, the operational amplifier circuit 57, in addition to having an operational amplifier A1, further includes three resistors R1, R2 and R3 (having values of 10 Kohms, 10 Kohms and 100 Kohms, respectively) and a capacitor C1 (having a value of 100 pF). The operational amplifier circuit 58, in addition to having an operational amplifier A2, further includes three resistors R4, R5 and R6 (having values of 10 Kohms, 4.7 Kohms and 47 Kohms, respectively), and a capacitor C2 (having a value of 100 pF).

The operational amplifier circuit 58, in addition to receiving the second signals by way of the connection 59, also receives signals from the potentiometers 46,48 by way of the links 50. Based upon the signals from the potentiometers 46,48, the operational amplifier circuit 58 modifies the zero level and the gain of the second signals to arrive at third signals that are provided to a sample and hold circuit 60 by way of a connection 61. The operational amplifier circuits 57,58 together in part serve to reduce noise in the signals from the oxygen sensing device 28.

The sample and hold circuit 60 constitutes one embodiment of the memory device 55 shown in FIG. 1. In the particular embodiment shown, the sample and hold circuit 60 includes a LF398 AN sample and hold monolithic integrated circuit chip ("LF398 S&H") available from National Semiconductor Corp. of Santa Clara, Calif. The sample and hold circuit 60, in addition to having the LF398 S&H additionally includes, as shown, six resistors R7, R8, R9, R10, R11 and R12 (having values of 20 Kohms, 1 Mohm, 100 Kohms, 1.78 Kohms, 4.65 Kohms and 1 Kohm, respectively) and a capacitor C3 (having a value of 0.2 microFarads).

As shown, the sample and hold circuit 60 is also coupled to the links 54 so as to receive signals from the sample and hold switch 52 indicative of when that switch is pressed or triggered. When a signal provided via the links 54 to the sample and hold circuit 60 indicates the triggering of the sample and hold switch 52, the sample and hold circuit 60 records (at least temporarily) the value of the third signal as provided via the operational amplifiers 57,58 at that time. Further, the sample and hold circuit 60 also then provides onto the communication links 44 a corresponding signal indicative of the third signal (which is also indicative of the received value of the first signal) to cause an appropriate output by the voltmeter 42. Given the fast (nearly instantaneous) operation of the oxygen sensing device 28 and the other components, information regarding alveolar gas levels can be obtained and output in real-time (or almost in real-time).

In the present embodiment, the portable device 2 operates as follows. A patient or subject, starting at rest and breathing normally for about a minute, then places his or her mouth onto a disposable mouthpiece (not shown) at the inlet 6 of the receiving structure 4 and gives a single, fairly rapid (but not maximal) expiration breath. As the patient expires into the receiving structure 4, the breath passes through the inlet 6, through the valves 12 and 14, and finally out the outlet 8. At the beginning of the expiration, the air passing out of the patient's mouth and into the receiving structure 4 has a level of oxygen gas that reflects the mixed gases within the bronchial passages of the patient, but as the expiration proceeds towards its end, the oxygen gas level (and/or certain other gas levels such as the carbon dioxide level) tends to plateau at a particular level, e.g., at a relative minimum or maximum. This plateau level is indicative of the oxygen gas level within the alveoli of the subject.

As the patient finishes expiring, the valves 12 and 14 tend to close. This prevents air from the outside atmosphere from backing into the sampling space 10 by way of the outlet 8 due to inhaling by the patient or otherwise, which could reduce the accuracy of the results. Also, the closing of the valves 12,14 when the patient finishes expiring tends to trap a latter portion of the expired air within the sampling space 10. This trapped latter portion of the air is largely if not entirely representative of the alveoli gas rather than the mixed gases within the subject's bronchial passages.

It is at this time, when the latter portion of the expired air is trapped within the sampling space 10, that the patient or another person such as a technician, physician or nurse presses the sample and hold switch 52 that is coupled to the circuit board 30 by way of the communication links 54. The circuit board 30, which is continuously receiving signals provided from the oxygen sensing device 28 (which is continuously monitoring and sensing oxygen levels within the oxygen cell 18), then at that instant stores within a memory device 55 the current value of the first signal provided by way of the communication links 40. That stored value is what is used by the circuit board 30 as the output signal or signals provided by way of the communication links 44 to the voltmeter 42 (or other output devices).

Use of the sample and hold switch 52 in combination with the receiving structure 4 with the valves 12,14 facilitates the standardization of the exploratory procedure. In practice, it is fairly easy to assure that the sample and hold switch 52 is pressed within the relatively long period of time near the end of the expiration at which the valves 12,14 are effectively closed, and during which the gas levels within the sampling space 10 provided via the channel 16 to the oxygen cell 18 are representative of the alveolar gas levels (e.g., the plateau level of the oxygen gas has been attained).

In alternate embodiments, it is not necessary that command (s) be provided from a patient or other person by way of input devices such as the sample and hold switch 52. For example, in some embodiments, the circuit board 30 simply could detect by way of sensors when the valves 12,14 have closed, as an indication that a patient is completing an expiration and consequently that the gas within the sampling space 10 is representative of alveolar gas.

Also, in some other embodiments, the circuit board 30 has sufficient intelligence to monitor the signals arriving from the oxygen sensing device 28 to determine when the values that are being provided are likely to be indicative of the alveolar oxygen gas level. In particular, the circuit board 30 can have sufficient intelligence to determine when the plateau level is occurring as the patient continues to expire, thus indicating that the reading is representative of the alveolar gas level. Also, in some embodiments, the respiratory exchange ratio (R), which can be derived from the partial pressures of oxygen gas and carbon dioxide gas (when both gas levels are measured), is indicative of whether a patient/subject is in the required steady state.

FIGS. 1 and 2 show one particular circuit layout (complete with component values) that can be employed in the portable device 2 in accordance with one embodiment of the present invention. Nevertheless, it will be evident to those having ordinary skill in the art that, in alternate embodiments, a variety of other circuits, elements and components can be utilized, including, for example, programmable logic devices, microprocessors, other hard-wired circuitry, and other computer processing devices. Also, in further embodiments, certain of the components shown in FIGS. 1 and 2 can be integrated or divided into separate components in manners other than that shown. For example, the oxygen sensor circuit 26 could be combined onto the circuit board 30.

The particular components and component values employed in the portable device 2 also can be varied from those shown in FIGS. 1 and 2 depending upon the embodiment. For example, FIG. 2 shows that the operational amplifier circuits 57,58 include a variety of resistors and capacitors with specific component values, in addition to operational amplifiers. Yet these specific components and component values could be modified. For example, the resistor R4 of the operational amplifier circuit 58 that is coupled to the connection 59 could be modified in its resistance from the value shown in FIG. 2 (10 Kohms) to further modify the gain and, in certain embodiments, could be switched off and on.

Turning to FIGS. 3-4, additional information regarding the portable device 2 shown in FIGS. 1 and 2 is provided. In particular, FIGS. 3A, 3B, 3C, 3D and 3E show front elevation, left side elevation, right side elevation, bottom plan, and top plan views, respectively, of the portable device. As shown in FIGS. 3A-3E, the exterior of the portable device is a largely rectangular box 61 along one side of which is mounted the receiving structure 4. The device is relatively small and easily carried, having dimensions of about 10 inches by 9 inches by 2 inches. Also visible in certain of FIGS. 3A-3E, particularly the left side elevation view of FIG. 3B, are adjustment knobs of the potentiometers 46,48 as well as the power switch 34. Further, the right side elevation view of FIG. 3C reveals the sample and hold switch 52, and the front elevation view of FIG. 3A reveals the output display of the voltmeter 42. The output display can be, for example, a LCD alphanumeric display that provides, for example, digital numeric outputs.

Figure 4A:
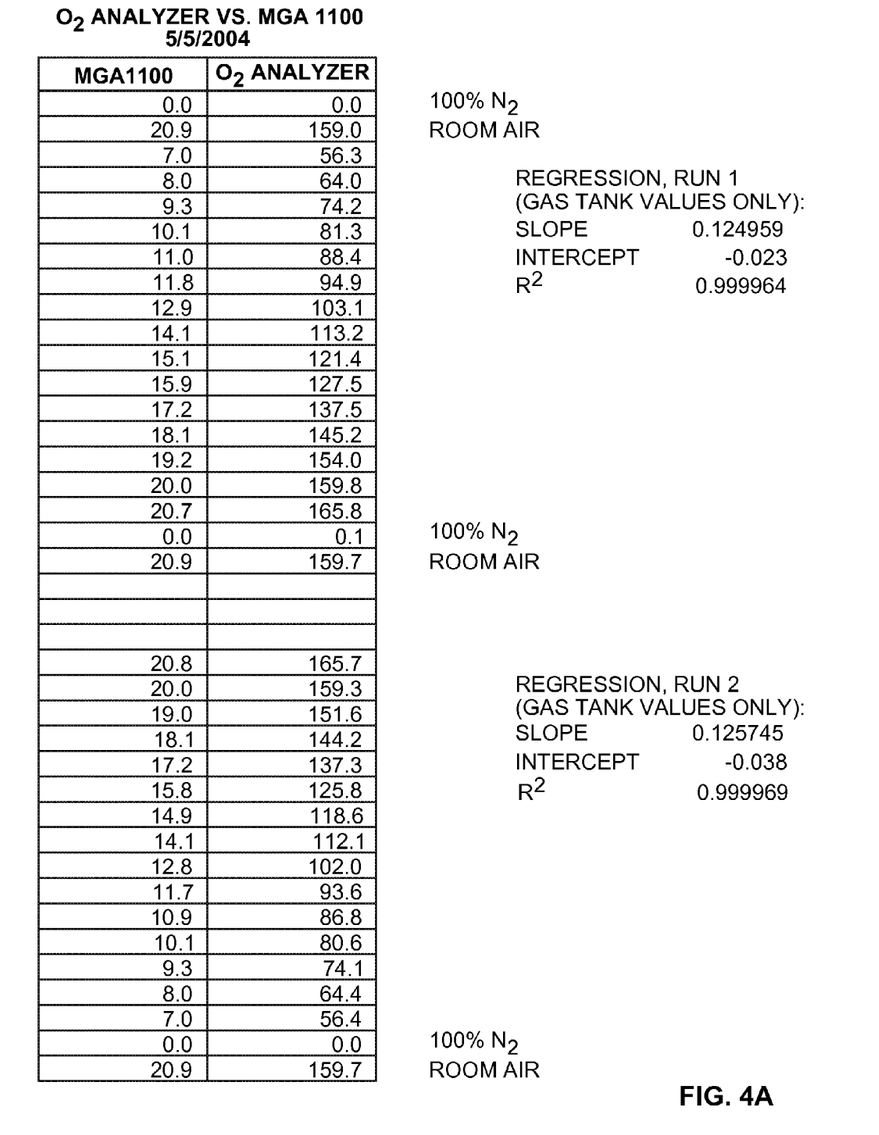
FIGS. 4A and 4B show in tabular and graphical form, respectively, exemplary comparative data concerning oxygen partial pressure measurements obtained using the exemplary meter of FIGS. 1-3 and a conventional MGA 1100 device.
Figure 4B:
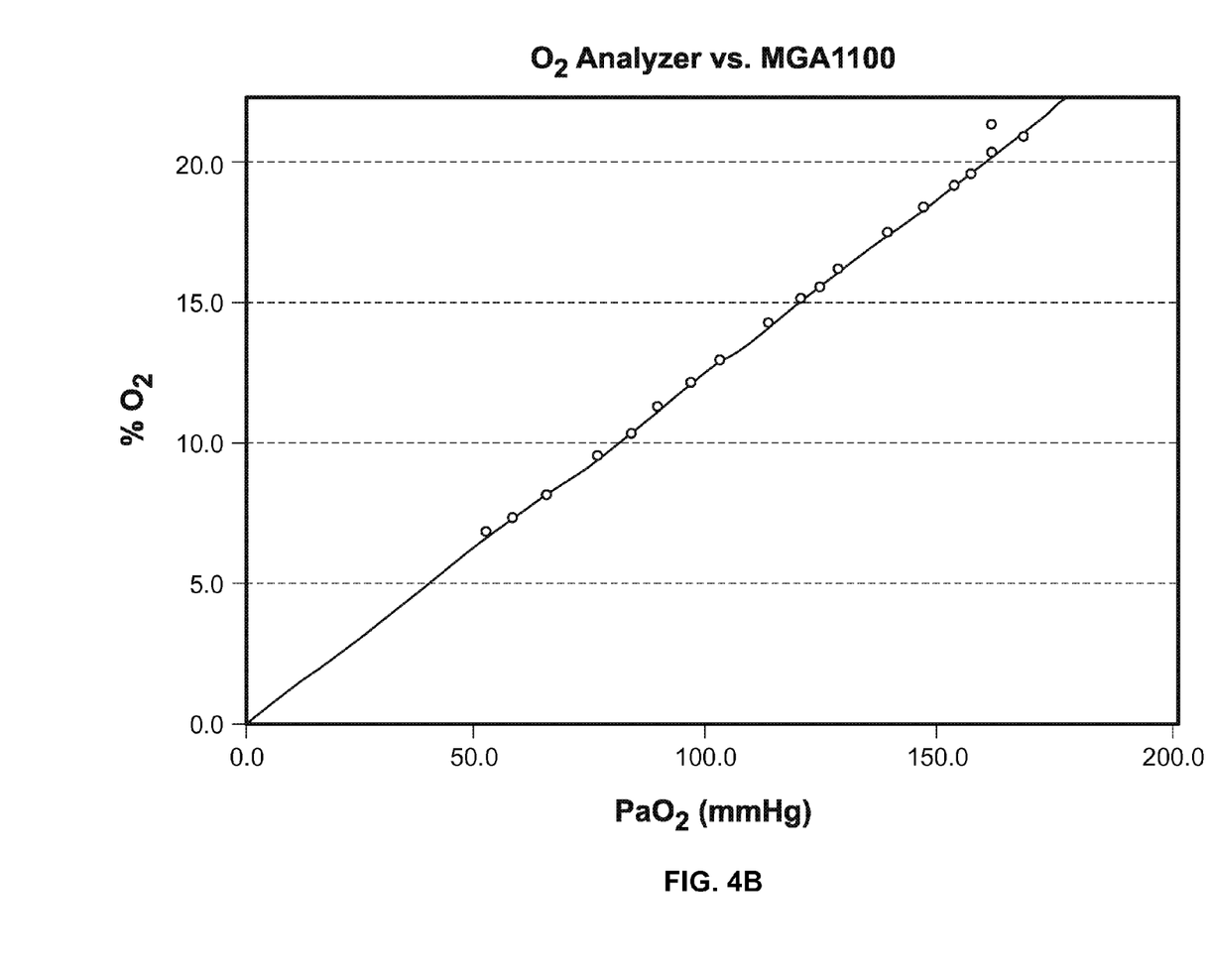

Additionally, FIGS. 4A-B show exemplary performance characteristics of the portable device 2 in measuring the partial pressure of oxygen in comparison with results obtained using a conventional system known as the MGA 1100 mass spectrometer manufactured by Marquette Electronics of Milwaukee, Wis. (now part of GE Healthcare). FIG. 4A shows the data in tabular form, while FIG. 4B shows the data in graphical form. As shown, the measured partial pressures of oxygen obtained by the portable device 2 are a good indication of the actual partial pressures of oxygen in the gas being sampled, as represented by the output of the MGA 1100 mass spectrometer.

Turning to FIGS. 5 and 6, a second, preferred embodiment of a portable device 102 in accordance with another embodiment of the present invention is shown. FIG. 5 in particular shows the portable device 102 in schematic form. As in the case of the portable device 2, the portable device 102 includes a tubular receiving structure 104 with an inlet 106 and an outlet 108 through which a patient or other subject would blow air/exhale as well as inhale. As shown, the receiving structure 104 preferably includes a disposable mouthpiece 110 that can be removed and discarded after use (for hygienic reasons). The disposable mouthpiece 110 can be an additional plastic tube that fits concentrically around an end of a main tubular portion 112 of the receiving structure 104 that is affixed to a main body 114 of the portable device 102. In contrast to the receiving structure 4, the receiving structure 104 does not include any valves such as the valves 12,14 that limit flow within that structure.

As shown, some of the air blown into the receiving structure 104 is conducted by way of a channel 116 into the main body 114 of the portable device 102. The air flows from the receiving structure 104 through the channel 116, in a direction indicated by arrows 120 and 124, into both an oxygen sensing device (or analyzer) 126 and a carbon dioxide sensing device (or analyzer) 128. The amount of flow is governed entirely or at least in part by a pump 122 that creates a partial vacuum causing the air to be pulled through the devices 126,128 and through the pump and subsequently forces the air out of the pump by way of a pump vent 129. As discussed above with respect to the channel 16, in certain embodiments the channel 116 can include or be formed by a drying tube commercially available from Perma Pure LLC of Toms River, N.J.

The oxygen sensing device 126 can take the form of the oxygen sensing device 28 shown in FIG. 1 (e.g., a UFO-130-2 sensor having both an oxygen cell and an oxygen sensor circuit) or some other form, and likewise the carbon dioxide sensing device can take any of a number of forms (e.g., a Jaeger HCS $CO_2$ sensor or Oridion $CO_2$ sensor including both a carbon dioxide cell and a carbon dioxide sensor circuit). As shown, the oxygen and carbon dioxide sensing devices 126, 128 are coupled to the circuit board 130 by way of links 138 and 140. The devices 126,128 are provided with power by way of the links 138, which relay power provided to the circuit board 130 from batteries 132 as determined by a power switch 134. Signals indicative of the levels of oxygen and carbon dioxide sensed by the sensing devices 126,128 are provided from those devices to the circuit board by the links 140.

In the embodiment shown, the main body 114 of the portable device 102 includes a port or plug 135 coupled to the batteries 132, at which power from another source can be provided to the portable device to allow for recharging of the batteries (as well as, in some embodiments, to allow for an alternate source of power to be supplied to the portable device). Additional links 136 also allow for power to be provided from the circuit board 130 to the pump 122. In the embodiment shown, the batteries 132 provide 5 Volt DC power, and such power is in turn provided to the circuit board 130, the devices 126,128 and the pump 122. However, in alternate embodiments, power with other characteristics could also be utilized.

The internal components of the circuit board 130 can vary depending upon the embodiment. In the embodiment shown, the 5 Volt power received from the power switch 134 can be directly provided to the sensing devices 126,128 and the sample pump 122, since each of those devices also requires 5 Volt power. Thus, in the embodiment shown, the circuit board 130 merely serves to directly connect the links 136,138 to the 5 Volt power received from the power switch, without any required DC-to-DC converter or other power converter. In alternate embodiments where the power requirements of the sensing devices 126,128 and/or the sample pump 122 differ from the characteristics of the power delivered from the batteries 132 via the power switch 134, one or more power conversion devices can be implemented on the circuit board.

In contrast to the portable device 2 of FIGS. 1-2, the portable device 102 of FIG. 5 does not output information by way of a voltmeter such as the voltmeter 42, but rather outputs information by way of a handheld computer 142 that is connected to the circuit board 130 by way of a serial communications link 144. The handheld computer 142 in various embodiments can take the form of any of a number of different devices. In a preferred embodiment, shown in FIGS. 5-6, the handheld computer 142 is a personal digital assistant such as a PalmPilot (made by PalmOne Inc., of Milpitas, Calif.). In alternate embodiments, the handheld computer 142 can be (or can be substituted with) a cellular telephone, a notebook computer, or another relatively small, portable computerized device.

Although the serial communications link 144 is shown in FIG. 5, the handheld computer 142 could also communicate with the main body 114 of the portable device 102 in other manners, for example, by way of wireless communications. In such embodiments employing wireless communications, the main body 114 of the portable device 102 would include a transmitter or transmitter/receiver for communications with the handheld computer 142, and would be capable of transmitting and/or receiving wireless signals in a manner appropriate for communication with the handheld computer. In further embodiments, the serial communications link 144 could be replaced with other, wired communication links, for example, links allowing for parallel communications.

Because the portable device 102 outputs data via the handheld computer 142, which is capable of storing large amounts of data received over long periods of time, the circuit board 130 does not include any sample and hold circuit for storing data, nor does the portable device 102 include any sample and hold switch or related potentiometers as in the case of the portable device 2. Rather, in the present embodiment, the portable device 102 merely includes an analog-to-digital converter 148 (shown in phantom), which converts the analog signals received from the sensing devices 126,128 via links 140 into digital signals that are provided to a RS-232 port 146. The digital signals provided to the port 146 in turn are provided to the handheld computer 142 via the serial communications link 144. In some embodiments, the analog-to-digital converter 148 is supplemented with other signal processing components that perform additional functions such as reducing noise.

As further shown in FIG. 5, the handheld computer 142 in the present embodiment receives the data signals from the communications link 144 and, in turn, stores the received data and displays the data in a graphical format on a display screen 150. When the handheld computer 142 is operating in a default mode, the display screen 150 provides first and second graphs 152 and 154, respectively, for displaying temporal variation in the partial pressures of oxygen and carbon dioxide, respectively. The displayed temporal variation in some circumstances can be provided in real time as the pressures of oxygen and carbon dioxide are measured by the sensing devices 126,128. Although graphical information is desirably output on the display screen 150, textual information also can be displayed. Further, in the embodiment shown, PB (barometric pressure) and $FO_2$ are also input into the handheld computer 142 when not in a default mode.

In addition to storing and graphically displaying information, the handheld computer 142 performs various additional functions. In particular, it is the handheld computer 142 that allows determinations to be made as to whether any given readings of oxygen or carbon dioxide gas levels are actually representative of alveolar gas levels rather than mixed, bronchial gases or other gases. The portable device 102 in contrast to the portable device 2 does not use any operator-triggered sample and hold circuit for recording gas levels that are sampled at particular operator-determined times, and further lacks any valves in the receiving structure 104 that might assist in localizing those amounts of expired gas that are most representative of alveolar gases.

Rather than employing these components, the portable device 102 with the handheld computer 142 makes available a largely continuous stream of data concerning gas levels over time, something which an operator or possibly even the handheld computer automatically can use to deduce alveolar gas levels. For example, where an operator (possibly but typically not the patient) is monitoring the graphically-output information on the handheld computer 142, the operator can request that the patient repeatedly breathe in and out through the receiving structure 104 while the operator monitors the output waveforms and the end-tidal values of those waveforms in particular. When these waveforms (particularly the end-tidal values) are largely steady, the patient is then asked to make a sudden full expiration. By again monitoring the output waveforms, the operator is then able to identify the alveolar gas levels, particularly the levels at which the gas levels plateau. Thus, the steady state information is used to determine when an expiration by the patient is representative of alveolar gases.

In addition to the aforementioned functions allowing for determinations to be made as to what gas level readings are representative of alveolar gas levels, the handheld computer 142 is in some embodiments also capable of other functions as well. For example, the handheld computer 142 in some embodiments allows for processing the received/stored data in a variety of ways and/or based upon a variety of different criteria. Further for example, maxima and minima of the oxygen and carbon dioxide readings could be obtained, or trends in the average values of the oxygen and carbon dioxide levels could be determined. Also, where oxygen levels are below an acceptable level, a warning indicator could be output. Additionally, in some embodiments, oxygen and carbon dioxide level data received by the handheld computer 142 can be utilized in conjunction with other information present within or received by the handheld computer from other sources (e.g., blood pressure information). Indeed, in some circumstances the handheld computer is the same handheld computer as is used by the operator for performing a variety of other tests or for other purposes.

Further, in some embodiments the handheld computer 142 not only receives information from the main body 114/circuit board 130 by way of the communications link 144, but also provides information to the main body 114/circuit board 130. For example, in some embodiments, the handheld computer 142 may provide pump control signals to the circuit board 130, which then influence operation of the pump 122. Where signals are sent to the main body 114/circuit board 130 by way of the communications link 144, the communications link is a bidirectional communications link. In further alternate embodiments, multiple communications links could be provided between the handheld computer and the main body 114.

Although not shown in FIGS. 5 and 6, the handheld computer 142 typically includes not only the display screen 150 for outputting information, but also includes an input device such as a keyboard or a pointing device or "wand" by which a user/operator is able to express commands, enter information, or make selections, for example, by selecting items within lists or menus displayed on the display screen 150. Through such user inputs, the manner of operation of the handheld computer 142 can be varied. For example, the manner in which data is graphically displayed on the display screen 150 can be changed. Also for example, the particular range of data displayed at any given time could be modified, for example, data concerning values of oxygen and carbon dioxide levels taken between specific points in time could be displayed.

Referring in particular to FIG. 6, a perspective view of the exterior of the portable device 102 of FIG. 5 is provided. As shown, the portable device 102 has a main housing 160 with dimensions of approximately 7 inches in length, 4 inches in width and 2 inches in depth. The receiving structure 104, with the disposable mouthpiece 110, is mounted on a top surface 161 of the main housing 160 and is removable for cleaning. The disposable mouthpiece 110 is, in the present embodiment, about 1 to 1½ inches long. As noted above, the receiving structure 104 does not include any valves such as the valves 12,14 discussed above, but rather merely includes a tubular or other unobstructed channel or cavity, which is linked to the sensing devices 126,128 by way of the channel 116 (see FIG. 5).

The main housing 160 further includes an indented portion 162 (indented with respect to the depth dimension) along which is mounted a case 164 within which is contained the handheld computer 142. The indented portion 162 of the housing 160 is also the portion of the housing that contains the oxygen and carbon dioxide sensing devices 126,128 as well as the sample pump 122 and the circuit board 130, while a non-indented portion 168 of the housing is the portion of the housing that includes the batteries 132, along with the power switch 134 (including an on/off status indicator such as a light-emitting diode 169) and the charging plug 135. The serial communications link 144 is shown to link the indented portion 162 with the handheld computer 142 by way of a port 172 within the case 164, which can be coupled to the normal synchronization port of the handheld computer.

Preferably, the case 164 is a rugged case that protects the handheld computer 142 from rain and other damage, that allows for easy insertion and removal of the handheld computer, and that includes an openable front window portion 166 that allows for user access of any buttons, keys or other input devices on the handheld computer 142. The display screen 150 is visible through the front window portion 166. Although preferably the case 164 allows for the use of a removable handheld computer 142, such that a dedicated computer is not required, in alternate embodiments the handheld computer 142 could be a dedicated computer that was permanently or semi-permanently attached to the case 164/housing 160.

The portable devices 2 and 102 shown in the FIGS. are only intended to be exemplary of a variety of different portable devices that are encompassed within the present invention. Depending upon the embodiment, the present invention can encompass devices that sense alveolar gas levels other than or in addition to the oxygen/carbon dioxide gas levels shown, and devices that make use of this data in a variety of ways. For example, in certain embodiments the circuit board 30 or the handheld computer 142 can calculate a respiratory exchange ratio (R), which provides information about the steady state breathing patterns of the patient. Also for example, depending upon the embodiment, the oxygen/carbon dioxide sensing devices 28, 126, 128 or other sensing device(s) need to be calibrated, and in certain applications such as high-altitude applications, the sensing devices can be calibrated by sampling dry ambient air since the partial pressure oxygen of dry ambient air is known if the barometric pressure is known.

The present invention is intended to encompass a variety of different portable devices that can be used to conduct noninvasive tests in a variety of different environments such as those discussed above, for example, in emergency departments of hospitals, paramedical ambulances, high altitude environments such as telescopic facilities, mines or other areas in which oxygen enrichment of the air as necessary, as well as in physical fitness/sports science environments involving high altitudes or other extreme conditions, for example, skiing, bicycle racing in high altitudes, scuba-diving, and other similar events.

In certain alternate embodiments, a somewhat elongated (e.g. 1 to 2 feet in length), flexible hose is used to couple the housings/main bodies of the portable devices with the tubular structures of the receiving structures 4,14 and thus with their mouthpieces (whether those mouthpieces are disposable or not). In some such embodiments, the flexible hoses can constitute the channels 16,116 (or portions thereof), and further sometimes can include or be formed through the use of the aforementioned Perma Pure drying tubes. When not in use with a patient or other subject, the tubular structures of the receiving structures 4,104 can be affixed to the housings/main bodies of the portable devices, for example, by way of spring clips.

However, when the portable devices are in use, the tubular structures can be disengaged from the housings/main bodies of the portable devices except insofar as they remain connected by way of the flexible hoses, and consequently the mouthpieces can be located somewhat apart from the housings/main bodies of the portable devices, and can be oriented in a variety of directions. Such embodiments allow for more comfortable use of the units during extended measurements, particularly for supine subjects. While intended primarily for use in measuring human alveolar gas levels, certain embodiments of the present invention also could be utilized with animals (e.g., by veterinarians).

It is specifically intended that the present invention not be limited to the embodiments and illustrations contained herein, but include modified forms of those embodiments including portions of the embodiments and combinations of elements of different embodiments as come within the scope of the following claims.

What is claimed is:

1. A portable alveolar gas measurement device comprising:
   a structure that receives a sample portion of breath, the structure comprising one or more valves that are configured to close and to thereby trap a latter portion of the breath;
   a first gas sensor in communication with the structure that detects a first gas level of a first gas within the sample portion and provides a first signal indicative of the first gas level;
   a handheld computer including circuitry coupled at least indirectly to the first gas sensor, wherein the circuitry is configured to receive at least one of the first signal and a second signal that is related to the first signal, and wherein the circuitry is configured to provide at least some assistance in determining whether a portion of information provided by the at least one of the first signal and the second signal is an indication of a first alveolar gas level; and
   an output device coupled to the circuitry and configured to provide an output indicative of the first alveolar gas level as determined at least in part with the assistance of the circuitry;
   wherein the handheld computer device includes a display as part of the output device,
   wherein the circuitry on the handheld computer device is configured to cause the display to provide a visual indication of variation of the first gas level over time based upon the at least one signal to allow a determination that a steady state breath pattern has occurred and as a result determine that the portion of information within the at least one signal is indicative of the first alveolar gas level,
   wherein the circuitry is configured to determine the portion of the information to be at least one value of the first signal obtained during a first time period; and
   wherein the circuitry includes an operator-actuatable switch and is configured to determine the first time period based upon a triggering of the switch.

2. The portable alveolar gas measurement device of claim 1, wherein at least one of the output device and another indicator associated with the output device serves as a warning indicator that provides a warning indication when the first alveolar gas level is in an abnormal range.

3. The portable alveolar gas measurement device of claim 1, wherein the first gas includes at least one of oxygen gas and carbon dioxide gas.

4. The portable alveolar gas measurement device of claim 3, wherein the first gas is one of oxygen gas and carbon dioxide gas, and wherein the first alveolar gas is the other of the oxygen gas and the carbon dioxide gas, wherein the first alveolar gas is calculated by the circuitry based at least indirectly upon the first signal indicative of the first gas.

5. The portable alveolar gas measurement device of claim 1, further comprising a second gas sensor in communication with the structure, the second gas sensor configured to detect a second gas level of a second gas within the sample portion and provide a third signal indicative of the second gas level.

6. The portable alveolar gas measurement device of claim 5, wherein the first signal is representative of a first partial pressure of oxygen gas and the third signal is representative of a second partial pressure of carbon dioxide gas.

7. The portable alveolar gas measurement device of claim 1, wherein the circuitry includes at least one of hardwired circuit componentry, a power converter, a microprocessor, a programmable logic device, a computer, an analog-to-digital converter, other means for processing, a sample and hold switch, a power switch, a power source, and a potentiometer, and wherein the gas sensor includes at least one of a gas sensing cell, a gas sensor circuit board, and a gas pump.

8. The portable alveolar gas measurement device of claim 1, wherein the structure is a tubular structure into which it is intended that at least one of a human subject and an animal subject at least one of exhale and inhale.

9. The portable alveolar gas measurement device of claim 8, wherein the one or more valves are configured to limit inflow of outside air in order to prevent contamination of the sample portion.

10. The portable alveolar gas measurement device of claim 8, wherein the structure includes a disposable mouthpiece portion.

11. The portable alveolar gas measurement device of claim 1, wherein the first gas sensor is coupled to the structure and at least some of the sample portion is caused to pass in proximity to the first gas sensor due to operation of a pump coupled to at least one of the gas sensor and the circuitry.

12. The portable alveolar gas measurement device of claim 1, wherein the device includes a housing within which is situated at least the first gas sensor, and an exterior case coupled to the housing, wherein the exterior case is configured to support at least one of a personal digital assistant, a handheld computer device, a cellular telephone, and another computerized device.

13. The portable alveolar gas measurement device of claim 1, wherein the switch is configured to be actuated by at least one of a human subject and an additional human being when the human subject has substantially fully expired a breath into the structure.

14. The portable alveolar gas measurement device of claim 13, wherein the switch is configured to cause a sample and hold circuit portion of the circuitry to at least one of store a current value of the first signal, process the current value of the first signal to obtain a related value, and output at least one of the current value and the related value as the second signal.

15. The portable alveolar gas measurement device of claim 14, wherein the circuitry is at least partly formed on a circuit board located within a housing that also supports the first gas sensor and the structure.

16. A portable alveolar gas measurement device comprising:
a structure that receives a sample portion of breath, the structure comprising one or more valves that are configured to close and to thereby trap a latter portion of the breath;
a first gas sensor in communication with the structure that detects a first gas level of a first gas within the sample portion and provides a first signal indicative of the first gas level;
a handheld computer including circuitry coupled at least indirectly to the first gas sensor, wherein the circuitry is configured to receive at least one of the first signal and a second signal that is related to the first signal, and wherein the circuitry is configured to provide at least some assistance in determining whether a portion of information provided by the at least one of the first signal and the second signal is an indication of a first alveolar gas level; and
an output device coupled to the circuitry and configured to provide an output indicative of the first alveolar gas level as determined at least in part with the assistance of the circuitry;
wherein the handheld computer device includes a display as part of the output device,
wherein the circuitry on the handheld computer device is configured to provide assistance in determining whether the portion of the information is used as an indication of the first alveolar gas level by monitoring variation of the first gas level over time based upon the at least one signal, determining when a steady state breath pattern has occurred, and subsequently determining that the portion of information within the at least one signal is indicative of the first alveolar gas level,
wherein the circuitry is configured to determine the portion of the information to be at least one value of the first signal obtained during a first time period; and
wherein the circuitry includes an operator-actuatable switch and is configured to determine the first time period based upon a triggering of the switch.

17. The portable alveolar gas measurement device of claim 16, wherein the portion of information concerns at least one of a relative minimum and a relative maximum of the second signal, and wherein the display of the output device is capable of providing at least one of graphical and alphanumeric information substantially in real-time.

18. The portable alveolar gas measurement device of claim 16, wherein the first gas sensor is configured to at least one of: continuously detect the first gas level and detect the first gas level at a particular determined time.

19. The portable alveolar gas measurement device of claim 18, wherein the first gas sensor is configured to continuously detect the first gas level and provide the first signal in response thereto.

20. The portable alveolar gas measurement device of claim 19, wherein the switch is configured to be actuated by at least one of a human subject and an additional human being when the human subject has substantially fully expired a breath into the structure.

21. The portable alveolar gas measurement device of claim 20, wherein the switch is configured to cause a sample and hold circuit portion of the circuitry to at least one of store a current value of the first signal, process the current value of the first signal to obtain a related value, and output at least one of the current value and the related value as the second signal.

22. The portable alveolar gas measurement device of claim 20, wherein the circuitry is at least partly formed on a circuit board located within a housing that also supports the first gas sensor and the structure.

23. The portable alveolar gas measurement device of claim 22, wherein the output device is a voltmeter supported along an exterior surface of the housing, and wherein the voltmeter is configured to display an output based upon the second signal, which is provided to the voltmeter by the circuitry.

24. The portable alveolar gas measurement device of claim 16, wherein at least one of the output device and another indicator associated with the output device serves as a warning indicator that provides a warning indication when the first alveolar gas level is in an abnormal range.

25. The portable alveolar gas measurement device of claim 16, wherein the first gas includes at least one of oxygen gas and carbon dioxide gas.

26. The portable alveolar gas measurement device of claim 25, wherein the first gas is one of oxygen gas and carbon dioxide gas, and wherein the first alveolar gas is the other of the oxygen gas and the carbon dioxide gas, wherein the first alveolar gas is calculated by the circuitry based at least indirectly upon the first signal indicative of the first gas.

27. The portable alveolar gas measurement device of claim 16, further comprising a second gas sensor in communication with the structure that is configured to detect a second gas level of a second gas within the sample portion and provide a third signal indicative of the second gas level.

28. The portable alveolar gas measurement device of claim 27, wherein the first signal is representative of a first partial pressure of oxygen gas and the third signal is representative of a second partial pressure of carbon dioxide gas.

29. The portable alveolar gas measurement device of claim 16, wherein the circuitry includes at least one of hardwired circuit componentry, a power converter, a microprocessor, a programmable logic device, a computer, an analog-to-digital converter, other means for processing, a sample and hold switch, a power switch, a power source, and a potentiometer, and wherein the gas sensor includes at least one of a gas sensing cell, a gas sensor circuit board, and a gas pump.

30. The portable alveolar gas measurement device of claim 16, wherein the structure is a tubular structure into which it is intended that at least one of a human subject and an animal subject at least one of exhale and inhale.

31. The portable alveolar gas measurement device of claim 30, wherein the one or more valves are configured to limit inflow of outside air in order to prevent contamination of the sample portion.

32. The portable alveolar gas measurement device of claim 30, wherein the structure includes a disposable mouthpiece portion.

33. The portable alveolar gas measurement device of claim 16, wherein the first gas sensor is coupled to the structure and at least some of the sample portion is caused to pass in proximity to the first gas sensor due to operation of a pump coupled to at least one of the gas sensor and the circuitry.

34. The portable alveolar gas measurement device of claim 16, wherein the device includes a housing within which is situated at least the first gas sensor, and an exterior case coupled to the housing, wherein the exterior case is configured to support at least one of a personal digital assistant, a handheld computer device, a cellular telephone, and another computerized device.

35. A method of determining at least one alveolar gas level of a human subject, the method comprising:
    transporting a portable device for determining the at least one alveolar gas level from a first location to a second location proximate the human subject;
    receiving a breath of the human subject within a receiving structure of the device to obtain a sample portion of the breath;
    operating a sensor in the device to sense a first gas level associated with the sample portion;
    providing a signal representative of the sensed first gas level;
    providing an output based at least indirectly upon the signal, wherein at least a part of the output is indicative of a first alveolar gas level of the human subject; and
    determining at least one of: whether a portion of information contained in the signal is used as an indication of the first alveolar gas level of the human subject; and whether the part of the output is indicative of the first alveolar gas level,
wherein the determining includes:
    observing the output;
    ascertaining when the output is representative of a steady breathing pattern;
    causing the human subject to provide an additional expiration into the receiving structure; and
    identifying the part of the output corresponding to a time period during the additional expiration as being indicative of the first alveolar gas level.

36. The method of claim 35, wherein the determining includes:
    observing that the human subject has substantially completed an expiration into the receiving structure; and
    receiving a trigger signal from a sample-and-hold switch when the expiration has been substantially completed, wherein the trigger signal from the switch precipitates recordation of the portion of information within a sample and hold circuit.

37. The method of claim 35,
wherein the output is at least one of a graphical output provided by way of a handheld computer and an alphanumeric output provided by way of a voltmeter.

38. The method of claim 35,
wherein at least one of the following is true:
the first alveolar gas level concerns a first gas and the first gas level concerns a second gas; and
an additional output is provided that is indicative of a second alveolar gas level, wherein the first alveolar gas level is an oxygen gas level and the second alveolar gas level is a carbon dioxide gas level.

* * * * *